United States Patent [19]

Frei

[11] 4,362,989
[45] Dec. 7, 1982

[54] PROCESS AND APPARATUS FOR CONTROLLING THE CONCENTRATION OF SOLID PARTICLES IN SUSPENSION IN A LIQUID FLUID

[75] Inventor: Charles Frei, Geneva, Switzerland

[73] Assignee: Ateliers des Charmilles S.A., Geneva, Switzerland

[21] Appl. No.: 203,719

[22] Filed: Nov. 3, 1980

[30] Foreign Application Priority Data

Nov. 16, 1979 [CH] Switzerland .................. 10237/79

[51] Int. Cl.³ .................................. G01N 27/00
[52] U.S. Cl. .......................... 324/71 CP; 324/450
[58] Field of Search ............ 324/71 R, 71 PC, 439, 324/442, 448, 450

[56] References Cited

U.S. PATENT DOCUMENTS 3,628,139 12/1971 Huber ........................ 324/71 CP
3,758,851 9/1973 Yokogama .................. 324/71 CP Primary Examiner—Michael J. Tokar
Attorney, Agent, or Firm—Hauke and Patalidis

[57] ABSTRACT

A process and apparatus for monitoring the concentration of electrically conductive solid particles in suspension in a fluid by circulating the fluid between a pair of electrodes opposed surfaces disposed at a fixed distance from each other, the electrodes being connected across a DC power supply. Electrical discharges occur across the gap between the electrodes, and the concentration of solid particles is determined as an inverse function of the average delay time interval required for triggering the electrical discharges, which is in turn measured by counting the number of electrical discharges occurring within a predetermined time interval.

6 Claims, 3 Drawing Figures

FIG. 1
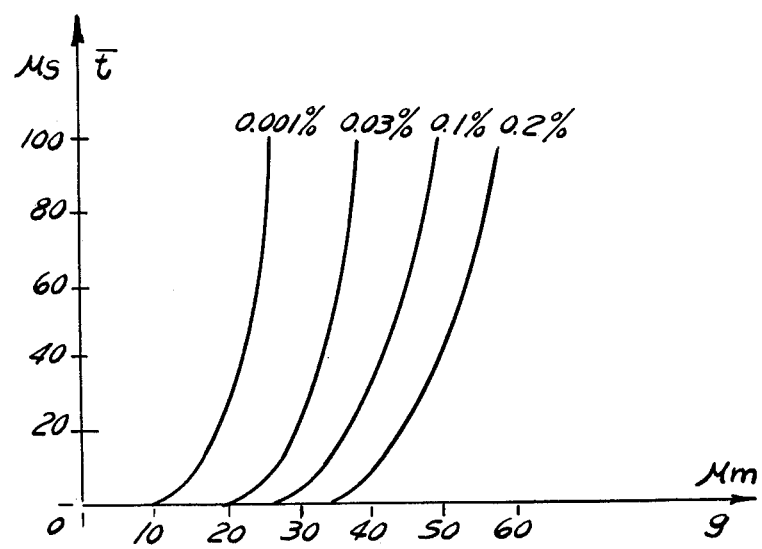
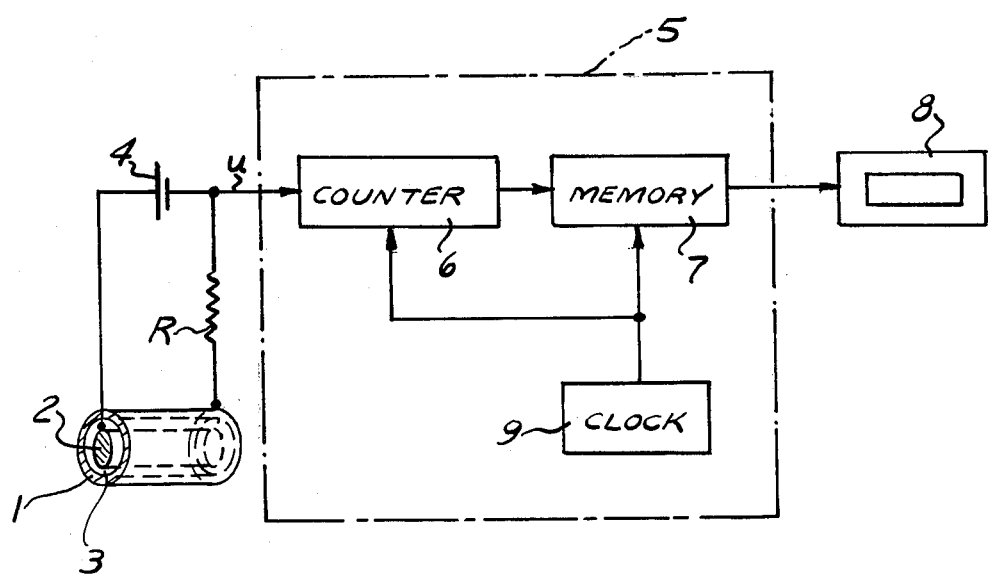
FIG. 2

PROCESS AND APPARATUS FOR CONTROLLING THE CONCENTRATION OF SOLID PARTICLES IN SUSPENSION IN A LIQUID FLUID

BACKGROUND OF THE INVENTION

The present invention relates to a process and apparatus for controlling the concentration of solid particles suspended in a liquid.

An adequate control of the concentration of solid particles in suspension in a liquid is particularly necessary in connection with electrical discharge machining of an electrode workpiece by means of an electrode tool, with a machining fluid flowing between the electrodes. Solid particles in the machining fluid, whether they are a by-product of the electrical discharge machining or from the dust suspended in the ambient, have a great influence upon the triggering of the electrical discharges. It is known that electrical discharge machining becomes more effective if the concentration of solid particles in the machining fluid reaches a predetermined rate. It is therefore important to control with precision the rate of concentration of solid particles in the machining fluid such as to maintain a maximum machining efficiency. Several methods have already been suggested for measuring and controlling the pollution of the fluid used for electrical discharge machining, for example by measuring the light absorption of the fluid by optical means. However, such methods are not very precise and are poorly suited to measure the small concentrations of solid particles which are rather common during electrical discharge machining.

SUMMARY OF THE INVENTION

The process and apparatus of the invention have for principal object to determine and measure the concentration of solid particles in suspension in an EDM machining liquid fluid with high precision and over a very wide concentration range. The invention has for principal object to cause flow of the machining fluid between a pair of electrodes having opposed active surfaces of predetermined areas, while maintaining the active surfaces at a constant distance from each other, to effectuate electrical discharges between the electrode surfaces and to control a value representing the delay of triggering of the electrical discharges.

The diverse objects and advantages of the present invention will become apparent to those skilled in the art when the following description of the best mode contemplated for practicing the invention is read in conjunction with the accompanying drawing showing, for illustrative purpose, an example of apparatus according to the present invention, and the mode of operation of such apparatus for use in conjunction with an EDM apparatus. In the drawing:

BRIEF DESCRIPTION OF THE DRAWING

FIG. 1 is a graph representing the basic principles used for measuring concentration of solid particles in an EDM machining fluid;

FIG. 2 is an example of structure for measuring such a concentration; and

DETAILED DESCRIPTION OF THE PREFERRED EMBODIMENTS

Figure 3:
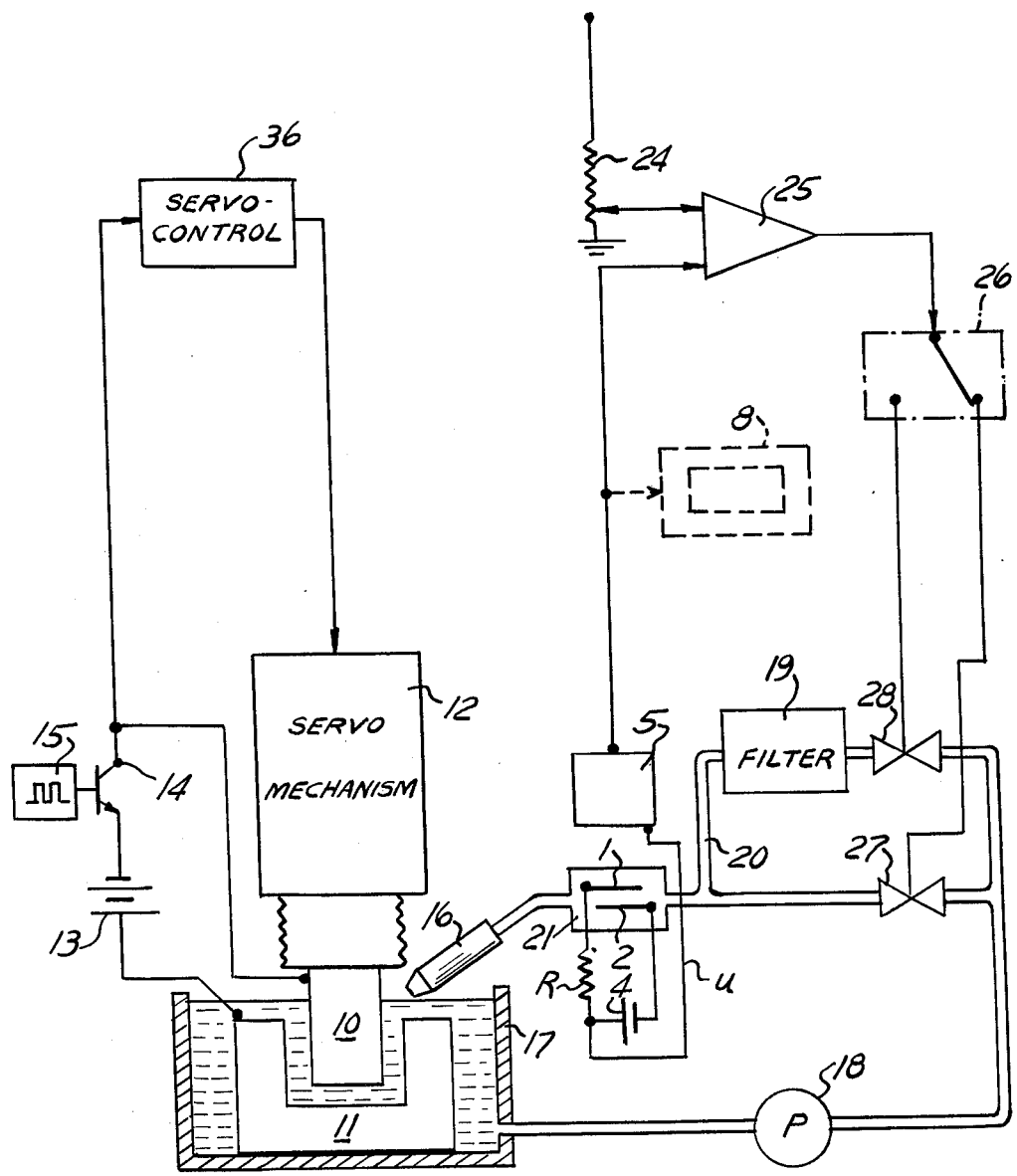
FIG. 3 is an example of EDM apparatus utilizing the arrangement of FIG. 2.

FIG. 1 is a diagram graphically illustrating the variation of the average delay of electrical discharge triggering between two electrodes through a dielectric fluid, as a function of the gap between the electrodes, for different values of concentration of solid particles in suspension in the fluid expressed in percent of unit of volume of the fluid. The triggering delay is the time interval between the instant at which voltage is applied across the electrodes and the instant at which an electrical discharge begins. It has been observed that for a constant given gap g between the electrodes, the electrical discharge average triggering delay $\bar{t}_D$ varies as an inverse function of the concentration of solid particles in the machining fluid. However, the average delay also varies as a function of the area of the active surface of the electrodes and as a function of the voltage amplitude causing the electrical discharges. In order for the diagram of FIG. 1 to be useful as a measure of particle concentration, it is necessary to maintain the other two variables, electrode active surface area and voltage amplitude, constant. If the two last mentioned parameters are maintained constant, it is clear from the diagram that an appropriate range of average trigger delay $\bar{t}_D$ may be chosen by selecting a value of the gap g for a given concentration range, the triggering delays being expressed in microseconds and the gap expressed in microns.

FIG. 2 is a block diagram of an arrangement for measuring the concentration of solid particles. A first electrode 1, in the form of a tube for example, contains a second electrode 2 in the form of a solid cylinder or rod, the second electrode 2 being disposed coaxially to the first electrode 1 and the outer surface of the inner, or second electrode 2 being at a constant predetermined distance or gap from the internal surface of the first, or outer, electrode 1. Those electrodes 1 and 2 are placed in the machining fluid circuit, not shown, such as to cause the machining fluid to flow through the gap 3 between the electrodes. A DC power supply 4 is connected across the electrodes 1 and 2 through a resistor R of a value high enough to prevent electrical discharges, triggered by applying the voltage of the DC power supply 4 across the electrodes, from becoming self-sustaining and for not causing any electrical discharge machining of the electrodes. The electrical discharges, which in reality are microdischarges, appear across the resistor R in the form of voltage pulses u of very short duration.

It is evident that, in view of the capacitance between the surfaces of the electrodes 1 and 2, the voltage between the electrodes increases progressively after each microdischarge, because the capacitor formed by the electrodes must be charged through the resistor R. The time interval between two consecutive microdischarges therefore increases as a function of the triggering delay, such that the number of microdischarges per unit of time provides a means for measuring the average triggering delay of the microdischarges. The number of microdischarges is calculated by the circuit 5, FIG. 2, which comprises a counter 6 having an input connected to the common terminal of the DC power supply 4 and of the resistor R. The number of discharges counted by the counter 6 is stored in the memory 7 which, in turn, supplies the count to a visual display 8. A constant frequency oscillator, or clock 9, is connected to the counter 6 and to the storage memory 7, such as to provide predetermined constant time intervals, on one hand to store the number of microdischarges during such a pre-determined time interval and on the other hand to re-set the counter 6 to zero.

The electrodes illustrated at FIG. 2 could have a different shape, for example they could be conical or flat, such as to permit adjusting the electrical discharge gap as a function of the solid particle concentration level. A similar method for measuring the solid particle concentration could be used by replacing the electrodes of FIG. 2 by the electrodes formed by the electrode workpiece and the electrode tool of an EDM apparatus. In such a structure, measuring can be effected only after rough machining, in the course of a finish machining pass, when the area of the surface of the electrode workpiece subjected to electrical discharges remains substantially constant. It would be necessary, in addition, to use a servo control of the electrode tool or of the workpiece designed for maintaining the machining gap at a strictly constant value in the course of a machining pass, for example by adjusting the feed of the electrode tool such as to maintain the voltage level of the machining electrical discharges at a constant value. Such an arrangement, however, presents the advantage of measuring the concentration of solid particles exactly at the location or zone where machining is effected.

FIG. 3 illustrates an example of EDM apparatus whose machining fluid is controlled according to the invention.

An electrode tool 10 is displaced relative to an electrode workpiece 11 by means of a servo mechanism 12. Machining electrical discharges are obtained from a DC power supply 13 through an electronic switch 14 controlled by a pulse generator 15. The servo mechanism 12 is controlled by a control circuit 36 such as to maintain predetermined machining conditions between the electrode tool 10 and the workpiece 11.

The machining fluid is supplied to the machining zone between the electrode tool 10 and the workpiece 11 by a nozzle 16 and flows into a tank 17 in which the electrode workpiece 11 is mounted. The circuit through which the machining fluid circulates comprises a pump 18, a filter 19 disposed in a bypass 20 and an arrangement for measuring the concentration of solid particles comprises a chamber 21 in which are disposed the measuring electrodes 1 and 2, fixedly mounted at a predetermined distance from each other within the chamber 21 connected to the nozzle 16 upstream of the nozzle.

As previously described in relation to FIG. 2, electrical discharges occurring at a low energy level between the electrodes 1 and 2 are obtained from a DC power supply 4 through a resistor R and a measuring circuit 5, similar to the circuit 5 of FIG. 2, provides at its output a signal representative of the average number of discharges during a predetermined time interval. This signal is compared to a reference signal obtained from a potentiometer 24 in an op-amp comparator 25 whose output signal controls, through a relay switch 26, either a valve 27 which, when open, causes direct flow of the machining fluid to the machining zone, or a valve 28 which, when open, causes the machining fluid to flow through the filter 19 such as to supply filtered machining fluid to the machining zone, according to the value of the signal at the output of the comparator 25. Such an arrangement permits to control with precision the concentration of solid particles in the machining fluid supplied to the machining zone.

Measuring the concentration of solid particles can also be made downstream of the machining zone between the tank 17 and the pump 18, or at the outlet of a channel withdrawing the fluid from the machining zone, such channel being disposed through one or the other of the electrodes 10 and 11.

Although the present invention has been described with respect to its application to electrical discharge machining, it will be readily apparent to those skilled in the art that the invention has many useful applications other than in EDM. For example, the invention can be used for controlling the concentration in metallic chips or particles in the coolant or other machining fluid used during conventional machining by a machine tool. The concentration in chips or metallic particles can be used, for example, to adjust the coolant or machining fluid flow rate. In a similar manner, in applications to stationary or motor vehicle internal combustion engines, the concentration of electrically conductive solid particles in the lubricant can be periodically or continuously monitored, such as to determine the amount of pollution of the lubricant requiring an oil change.

The pollution detecting electrode 2 can be in the form of a wire, as the electrode wire used in travelling wire electrode EDM apparatus. The tubular electrode 1 is disposed peripherally to the wire proximate the machining zone, for example proximate the outlet of a nozzle supplying machining fluid to, or withdrawing machining fluid from, the machining zone. In such manner, a very precise control of the concentration of solid particles in suspension in the machining fluid is achieved.

Having thus described the present invention by means of typical examples of structure for practicing the invention, modifications whereof will be apparent to those skilled in the art, what is claimed as new is as follows:

1. A process for controlling the concentration of electrically conductive solid particles in suspension in a liquid fluid, said process comprising flowing said liquid fluid between a pair of electrodes each having an active surface of predetermined area, maintaining said active surfaces at a constant distance from each other, connecting said electrodes across a D.C. power supply such as to cause relatively low energy electrical discharges to occur between said active surfaces, and determining the average delay time interval between applying a predetermined voltage between said electrodes and the occurrence of an electrical discharge, whereby the duration of said average delay time interval is an inverse function of the concentration of said solid particles in said liquid fluid.

2. The process of claim 1 wherein said average time delay interval is determined by counting the number of electrical discharges occurring within a predetermined time period.

3. An apparatus for measuring the concentration of electrically conductive solid particles in suspension in a liquid fluid, said apparatus comprising a pair of electrodes having each an active surface of predetermined area disposed at a predetermined distance from a corresponding active surface of predetermined area of the other electrode, means for flowing said liquid fluid between said electrodes, means for applying a DC voltage across said electrodes for causing low energy electrical discharges to occur between said electrodes, and means for developing a signal representative of the average delay time interval of triggering of said electrical discharges.

4. The apparatus of claim 3 wherein said measuring circuit comprises means for counting the number of electrical discharges during a predetermined time interval.

5. The apparatus of claim 3 wherein said electrodes comprise a tubular member defining one of said electrodes and a cylindrical member defining the other of said electrodes disposed coaxially to said tubular member.

6. The apparatus of claim 5 wherein said measuring circuit comprises means for counting the number of electrical discharges during a predetermined time interval.

* * * * *